United States Patent
Barer et al.

[11] 3,943,253
[45] Mar. 9, 1976

[54] GUANIDO ACIDS AS FUNGICIDES

[76] Inventors: Sol J. Barer, 18-01 Fox Run Drive, Plainsboro, N.J. 08536; Patti L. Kostrzewski, 301 Maple Ave., North Plainfield, N.J. 07060

[22] Filed: June 27, 1974

[21] Appl. No.: 483,580

[52] U.S. Cl. ............ 424/319; 260/534 R; 424/315; 424/318; 424/DIG. 8
[51] Int. Cl.² ............... A01N 9/20; A01N 9/24
[58] Field of Search ............. 424/318, 319, DIG. 8; 260/534 R

[56] References Cited
UNITED STATES PATENTS

| | | | |
|---|---|---|---|
| 1,967,400 | 7/1934 | Fischl | 260/534 |
| 2,654,779 | 10/1953 | Vassel et al. | 260/534 |
| 2,759,017 | 8/1956 | Vassel et al. | 260/534 |
| 2,761,807 | 9/1956 | Borsook et al. | 424/319 |
| 2,820,822 | 1/1958 | Skelly | 260/534 |

*Primary Examiner*—Frederick E. Waddell
*Assistant Examiner*—Allen J. Robinson
*Attorney, Agent, or Firm*—Cushman, Darby and Cushman

[57] ABSTRACT

Compounds of the formula

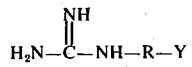

wherein R is $C_nH_{2n}$ and wherein $n$ is an integer of 1 to 11, and wherein Y is the sulfonic acid ($-SO_3H$) group or carboxylic acid ($-CO_2H$) group, have been found to have fungicidal activity. The compounds can be used in the free acid or salt form.

4 Claims, No Drawings

GUANIDO ACIDS AS FUNGICIDES

The present invention relates to the use of guanido compounds as fungicides. They are effective against a broad range of fungi and can be used, for example, as protectant foliar fungicides and as systemic fungicides, while having little phytotoxic activity.

The compounds employed in the present invention have the formula

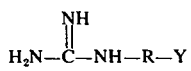

wherein R is $C_nH_{2n}$, and wherein $n$ is an integer of 1 to 11, preferably from 1 to 7, and wherein Y is a sulfonic acid ($-SO_3H$) group or carboxylic acid ($-CO_2H$) group. There can also be used salts thereof.

Guanido acids per se are known in the art. They can be prepared for example in the manner shown in Garst U.S. Pat. Nos. 2,766,282, Vassel, 2,654,779, Vassel, 2,759,017, Brand et al., *Org. Synth. Vol.* 22, page 59 et seq., (1942), Walter, *Angew. Chem. Vol.* 67, page 275 et seq., (1955), Fasold et al, *Biochem Z., Vol.* 335, page 86 et seq., (1961), Makisumi, *J. Biochem.* (Tokyo) Vol. 49, page 284 et seq., (1961) and Cramer *Chem. Br. Vol.* 92, page 392 et seq. (1952). The compounds can also be prepared as shown in Examples 1 and 2 below.

Examples of suitable guanido compounds for use in the invention include glycocyamine, N-methyl-glycocyamine (creatine), caprocyamine, alpha-guanido-n-butyric acid, alpha-guanido-propionic acid, valerocyamine, omega-guanido-pelargonic acid, omega guanido lauric acid, omega-guanido-decanoic acid, taurocyamine, guanido-methanesulfonic-acid, alpha-guanido-propanesulfonic acid, 3-guanido-propanesulfonic acid, 4-guanido-n-butanesulfonic acid, 6-guanido-hexanesulfonic acid, 8-guanido-octanesulfonic acid, 10-guanido-decane-sulfonic acid, 11-guanido-undecanesulfonic acid.

There can also be used any of the conventional salts wherein the hydrogen atom of the carboxyl acid or sulfonic acid group is replaced by a metal, an ammonium or an amine group. Thus, there can be used, for example, salts of an alkali metal, e.g., sodium, potassium or lithium or of an alkaline earth metal, e.g., magnesium, calcium or barium or an ammonium salt or a salt of an amine, e.g., of the formula:

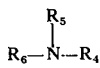

where $R_4$, $R_5$ and $R_6$ may be the same or different and are suitably hydrogen, alkyl of up to 18 carbon atoms, e.g., methyl, ethyl, propyl, butyl, hexyl, decyl, dodecyl, hexadecyl, octadecyl, isopropyl, isodecyl, or aryl, e.g., phenyl or tolyl, hydroxyalkyl, e.g., hydroxyethyl and hydroxylpropyl. Suitable amines include: ammonia, alkanolamines, such as diethanolamine, triethanolamine, ethanolamine, dipropanolamine, isopropanolamine, dimethylamine, triethylamine, trimethylamine, methylamine, ethylamine, diethylamine, dibutylamine, octadecylamine, hexadecylamine, tributylamine, aniline, methylphenylamine, diphenylamine, dimethylphenylamine, triphenylamine, N-methylaniline, p-methylaniline, dodecylamine.

Specific salts include, for example, the sodium salt of caprocyamine, sodium salt of taurocyamine, potassium salt of caprocyamine, potassium salt of taurocyamine, calcium salt of caprocyamine, calcium salt of taurocyamine, dimethylamine salt of caprocyamine, dimethylamine of taurocyamine, ammonium salt of caprocyamine, ammonium salt of taurocyamine.

The salts can be prepared in conventional fashion, e.g., the dimethylamine salt can be formed by allowing the free caprocyamine or taurocyamine to stand in excess liquid dimethylamine, e.g., at 0°–5° C. or the sodium salt can be prepared by mixing a solution of caprocyamine or taurocyamine in methyl alcohol with a solution of sodium hydroxide in methyl alcohol.

The fungicides and insecticides of the present invention can be used alone or they can be applied together with inert solids to form dusts, or can be suspended in a suitable liquid diluent, e.g., organic solvents or water.

There can also be added surface active agents or wetting agents and/or inert solids in the liquid formulations. In such case, the active ingredient can be from 0.01 to 95 percent or more by weight of the entire composition.

As organic solvents there can be employed hydrocarbons, e.g., benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol propylene glycol, butyl Carbitol acetate and glycerine, mixtures of water and organic solvents, either as solutions or emulsions, can be employed.

The compounds can also be applied as aerosols, e.g., by dispersing them in air by means of a compressed gas such as dichlorodifluoromethane or trichlorofluoromethane and other Freons and Genetrons, for example.

The compounds can also be applied with adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character. When a surface active agent is present, it is usually employed in an amount of 0.05 – 1% by weight.

Typical classes of surface active agents include alkyl sulfonate salts, alkylaryl sulfonate salts, alkylaryl polyether alcohols, fatty acids esters of polyhydric alcohols and the alkylene oxide addition products of such esters and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenyl condensed with 10 ethylene oxide units, soaps, e.g., sodium stearate and potassium oleate, sodium salt of propylnaphthalene sulfonic acid, di(2-ethylhexyl) ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (Nonionic 218), long chain ethylene oxide-propylene oxide condensation products, e.g., Pluronic 61 (molecular weight 1000), polyethylene glycol ester of tall oil acids, sodium octyl phenoxyethyoxyethyl sulfate, tris(polyoxyethylene) sorbitan monostearate (Tween 60), and sodium dihexyl sulfosuccinate.

The compounds can also be entrapped in water soluble hydrophilic homopolymers, e.g., polyvinylpyrrolidone, polyacrylamide or polymethacrylamide, or water soluble copolymers of these materials with hydroxyethyl acrylate, hydroxyethyl methacrylate, hydroxypropyl acrylate, hydroxypropyl methacrylate, as well as any of water soluble hydrophilic copolymers set forth in Gould U.S. Pat. No. 3,576,760, the entire disclosure of which is incorporated by reference. Thus the procedure of Gould Example 22 can be used replacing the 2,4- dichlorophenoxyacetic acid by one gram of the fungicidally active caprocyamine.

The guanido compounds can also be incorporated in photodegradable polymers such as polyethylene, polypropylene, polybutene or copolymers such as ethylene-propylene copolymers which are applied as agricultural mulches and used in pesticidal applications, especially fungicidal applications. Typical examples of suitable photodegradable polymer compositions include those set forth in Shepherd U.S. Pat. No. 3,590,528, Newland U.S. Pat. No. 3,592,792, Field U.S. Pat. No. 3,341,357, Moore U.S. Pat. No. 3,320,695, Newland U.S. Pat. No. 3,454,570, and German Offenlegungsschrift No. 2,158,379.

The guanido compounds of formulations containing same can also be admixed with hydrophilic polymers, either of the water-soluble or the water-insoluble type. Thus for controlled release of the fungicide of the present invention it can be entrapped in a hydrophilic polymer, e.g., in the form of a powder in the manner shown for medicines, flavors, fragrances, etc., in Shepherd U.S. Pat. No. 3,618,213. As hydrophilic polymers there can be used water-insoluble polymers of water-soluble hydroxyalkyl acrylates and methacrylates such as hydroxyethyl acrylate, hydroxypropyl acrylate, hydroxyethyl methacrylate, hydroxypropyl methacrylate, diethylene glycol monoacrylate, diethylene glycol monomethacrylate, dipropylene glycol monoacrylate, dipropylene glycol monomethacrylate or polymers of acrylamine, methacrylamide, vinyl pyrrolidone, and copolymers with polyethylenically unsaturated cross linking agents such as ethylene glycol dimethacrylate, ethylene glycol diacrylate, propylene glycol diacrylate, propylene glycol dimethacrylate, butylene dimethacrylate, divinyl benzene, triallyl melamine, N,N'-methylene bisacrylamide, pentaallyl sucrose, diallyl itaconate, allyl maleate, divinyl ether and others such as any of those set forth in Shepherd U.S. Pat. No. 3,575,123, col. 3, lines 15–35 for example. The cross linking agent can be present in an amount of 0.05% to 15% and upward to about 20%, usually 0.1 to 2.5% of the hydrophilic monomer.

There can also be included ethylenically unsaturated acids or salts thereof such as acrylic acid, cinnamic acid, methacrylic acid, itaconic acid, fumeric acid, maleic acid or partial esters such as 2-hydroxypropyl itaconate, 2-hydroxypropyl itaconate, 2-hydroxyethyl maleate, etc. There can also be used any of the other copolymerizable monomers set forth in the Shepherd patent the entire disclosure of which is hereby incorporated by reference.

The solid and liquid formulations can be prepared by any of the conventional procedures. For example, the compounds of the present invention can be applied to soil, growing plants, e.g., trees, cotton plants, wheat and other grain plants, vegetable plants, seeds, fabrics, etc., to give fungicidal protection.

The guanido compounds can be employed as fungicides and insecticides using effective amounts for the intended purpose. In general, these compounds can be employed at widely varying rates, e.g., 0.1 to 100 lbs/acre, usually 0.5 to 30 lbs/acre. As foliar fungicides they are usually employed at a dosage of 0.1 to 20 lbs/acre. As insecticides they are normally used in a dosage of 0.2 to 10 lbs/acre. When the compounds are used as fungicides or insecticides on growing crops, e.g., wheat, cotton, barley, soybeans, corn, oats, turnips, tomatoes, beans, peas, carrots, broccoli, beets, trees, etc., they should not be used in an amount to kill the plants. The compounds also can be applied to seeds, or fabrics, etc., as fungicides, bactericides or insecticides.

Unless otherwise indicated, all parts and percentages are by weight.

EXAMPLE 1

Preparation of Caprocyamine (I)

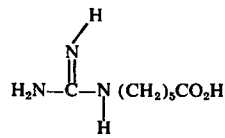

150 Grams of thiourea and 250 grams of ethyl bromide were warmed in 200 ml of absolute ethanol for 3 hours at 55°–65° C. Removal of the ethyl bromide and ethanol by vacuum distillation yielded II below in 90% yield.

252 Ml of 2N NaOH were added to 92.5 grams of compound II above in an ice bath, followed by the addition of 90 grams of caproic acid in 110 ml hot (85° C) H₂O. The flask was removed from the bath when the temperature reached 25° C. A white solid crystallized after approximately 3 hours (at 5° C.). Compound I (8% yield) was confirmed by elemental analysis for C, H, N, and Cl and by infrared spectroscopy.

EXAMPLE 2

Preparation of Taurocyamine (III)

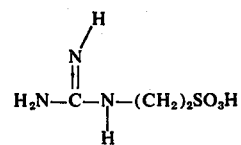

The above procedure of Example 1 was utilized with one modification. The solution of taurocyamine in $H_2O$ was allowed to stand for 24 hours in the refrigerator to effect crystallization. Compound III (50% yield) was confirmed by elemental analysis for C, H, N, and Cl and infrared spectroscopy.

The test compounds were made up as 50% wettable powders. Thus, the composition contained 50% of the Caprocyamine or Taurocyamine, 1.0% Igepan AP 78 (coconut oil ester of sodium isethionate) as a wetting agent, 1.0% Marasperse N-22 (sodium lignin sulfonate) as a dispersing agent and 48% of Microcel C as an inert filler.

In the foliar fungicide tests, the formulation was applied to the leaves of the plant and in the systemic fungicide test the formulation was applied to the ground in which the plants were growing.

The fungicidal activities reported below were obtained employing the following general test procedures:

TEST PROCEDURE FOR PROTECTANT FUNGICIDAL ACTIVITY AGAINST RICE BLAST DISEASE, Piricularia oryzae Rice plants in fully developed second-leaf growth stage are mounted on a compound turntable and sprayed at 40 pounds pressure for 60 seconds with the candidate compound at concentrations indicated. Approximately 150 ml of test solution are delivered. Candidate samples are prepared for spraying by dissolving in a suitable solvent (e.g., methyl alcohol) and diluting to desired concentration with deionized water containing wetting and dispersing agents.

After drying, treated plants are spray-inoculated at 30 pounds pressure with an aqueous spore suspension of Piricularia oryzae and then immediately placed in an incubation chamber maintained at 70° F and 95% plus RH. After proper incubation time plants are removed to the greenhouse for disease development. Infection lesions are sufficiently developed within 5 days after inoculation to permit assessment of control. Disease severity is determined by actual count of the number of infection lesions developing on untreated inoculated controls. Effectiveness of treatment is determined by direct comparison of the number of infection lesions appearing on the respective treated plants compared directly with those lesions appearing on untreated inoculated controls. PMA is used as a reference standard. All units of test include a minimum of three replicates.

TEST PROCEDURE FOR PROTECTANT FUNGICIDAL ACTIVITY AGAINST POWDERY MILDEW OF CUCUMBERS, Erysiphe cichoracearum Candidate compounds are prepared for spraying by dissolving in a suitable solvent (e.g., methyl alcohol) and diluting to desired concentration with deionized water containing wetting and dispersing agents.

Straight-eight cucumber (Cumcumis sativas) plants in first true leaf stage, approximately 14 to 18 days old, grown under greehouse conditions, are mounted on a compound turntable and sprayed to incipient run off at 30 psi with candidate compound at concentration indicated, using 30 ml of the spray solution per five replicates (equivalent to approximately 200 gpa).

After treated plants have dried, they are placed among diseased Erysiphe cichoracearum cucumber plants according to the pattern below, subjected to an initial spore shower by dusting with spores from diseased plants and then left undisturbed in place for approximately 10 days. By this procedure treated plants are subjected to the cited initial spore shower as well as to continuing natural infection pressure from surrounding inoculum. Observations 10 days after initial inoculation determine effectiveness of treatments. Untreated controls will generally reflect 75 to 100% leaf area diseased at this time. Effectiveness of treatment is determined by direct comparison of the average percentage leaf area infection on treated plants with the average percentage leaf area infection on untreated inoculated control. Karathane is used as a reference standard.

TEST PROCEDURE FOR PROTECTANT FUNGICIDAL ACTIVITY AGAINST LEAF RUST OF WHEAT, Puccinia rubigo-vera Cheyenne wheat plants, Triticum vulgare, approximately 7 to 8 days old and 4 to 5 inches tall are mounted on a compound turntable and sprayed at 40 pounds pressure for 60 seconds with respective candidate compounds at concentrations indicated. Candidate compounds are prepared for spraying by dissolving in a suitable solvent system, e.g., methyl alcohol and diluting to desired concentration with deionized water containing wetting and dispersing agents.

After drying, treated plants are dusted with spores of Puccinia rubigo-vera directly from diseased plants and then immediately placed in an incubation chamber maintained at 70° F and 95% plus RH. After the proper incubation period, plants are removed to the greenhouse for disease development.

Disease severity (infection pressure) is determined by actual count of developed pustules on inoculated but otherwise untreated controls. Control effectiveness is determined by actual count of the number of developed pustules appearing in the respective treatments compared directly to equivalent developed pustules developing on inoculated but otherwise untreated controls. Maneb is used as a reference standard. All units of test include a minimum of three replicates.

TEST PROCEDURE FOR PROTECTANT FUNGICIDAL ACTIVITY AGAINST BACTERIAL LEAF SPOT OF TOMATOES, Xanthomonas vesicatoria Bonny Best tomato plants approximately 6 to 7 weeks old, in six to seven-leaf growth stage, are mounted on a compound turntable and sprayed at 35 pound pressure for 50 seconds with the candidate compound as concentrations indicated. Approximately 150 ml of test solution is delivered. Candidate samples are prepared for spraying by dissolving in a suitable solvent (e.g., methyl alcohol) and diluting to desired concentration with deionized water containing wetting and dispersing agents.

After drying, treated plants are spray-inoculated at 30 pounds pressure with an aqueous cell suspension of Xanthomonas vesicatoria containing 5 percent Carborundum and then immediately placed in an incubation chamber maintained at 70° F and 95% plus RH. After 40 hours in the incubation chamber, plants are removed to the greenhouse for further development of infection lesions. Disease severity is determined by count of lesions present on six to seven treated leaves.

Effectiveness of treatment is determined by direct comparison with inoculated controls. Streptomycin sulfate is used as a reference standard.

TEST PROCEDURE FOR SYSTEMIC PROTECTANT FUNGICIDAL ACTIVITY AGAINST POWDERY MILDEW OF CUCUMBERS, *Erysiphe cichoracearum*

Straight-eight cucumber plants in first true leaf stage, approximately 14–18 days old, are used as host plants. Candidate compounds dissolved in a suitable solvent system, e.g., methyl alcohol and diluted to appropriate concentrations with deionized water are applied to the soil surface of respective containers of cucumber plants which in turn are returned to the greenhouse.

Two days after treatment subject plants are placed among diseased (*Erysiphe cichoracearum*) cucumber plants, according to the pattern below, subjected to an initial spore shower by dusting with spores from diseased plants and then left undisturbed in place for approximately 10 days. By this procedure treated plants are subjected to the cited initial spore shower as well as to continuing natural infection pressure from surrounding inoculum. Observations 10 days after initial inoculation determine duration of effectiveness of treatments. Untreated controls will reflect 75% to 100% leaf area diseased at this time. Effectiveness of treatment is determined by direct comparison with untreated inoculated controls. Benlate is used as a reference standard. All units of test include a minimum of three replicates. The results of the fungicidal tests are set forth in Example 3 and Example 4 below.

Plant injury in Examples 3 and 4 was measured on a 0–10 scale with 0 denoting no injury and 10 indicating phytotoxicity.

EXAMPLE 3: -Efficacy of Caprocyamine as a Fungicide

A. Foliar Fungicide  
Formulation: As a 50% wettable powder  
Concentration: 0.5 lb/acre

| Disease | % Disease Control: Plant Injury (0–10) |
|---|---|
| Powdery Mildew Cucumber *Erysiphe cichoracearum* | 27:0 |
| Leaf Rust Wheat *Puccinia rubigo-vera* | 83:0 |

B. Systemic Fungicide  
Formulation: As a 50% wettable powder  
Concentration: 10 lb/acre

| Disease | % Disease Control: Plant Injury (0–10) |
|---|---|
| Powdery Mildew Cucumber *Erysiphe cichoracearum* | 40:0 |
| Early Blight Tomato *Alternaria solani* | 26:0 |

EXAMPLE 4: -Efficacy of Taurocyamine as a Fungicide

A. Foliar Fungicide Activity  
Formulation: As a 50% wettable powder  
Concentration: 0.5 lb/acre

| Disease | % Disease Control: Plant Injury (0–10) |
|---|---|
| Powdery Mildew Cucumber *Erysiphe cichoracearum* | 33:0 |
| Leaf Rust Wheat *Puccinia rubigo-vera* | 44:0 |
| Bacterial Leaf Spot Tomato *Xanthomonas vesicatoria* | 67:0 |

B. Systemic Fungicidal Activity  
Formulation: As a 50% wettable powder  
Concentration: 10 lb/acre

| Disease | % Disease Control: Plant Injury (0–10) |
|---|---|
| Powdery Mildew Cucumber *Erysiphe cichoracearum* | 63:0 |
| Early Blight Tomato *Alternaria solani* | 11:0 |

What is claimed is:

1. A method of destroying fungi comprising applying to the fungi a fungicidally effective amount of a guanido compound of the formula:

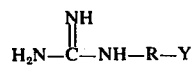

where R is $C_nH_{2n}$ and $n$ is an integer of 1 to 11 and Y is the group —COOH or a salt thereof.

2. The method of claim 1, wherein the guanido compound is caprocyamine.

3. The method of claim 1, wherein the guanido compound is applied to growing plants infested with the fungi.

4. The method of claim 1 wherein $n$ is 1 to 7.

* * * * *